United States Patent [19]

Nobles, Jr.

[11] Patent Number: 5,045,836
[45] Date of Patent: Sep. 3, 1991

[54] VEHICLE ANTI-FREEZE MONITOR

[76] Inventor: Eugene R. Nobles, Jr., 4184 Gwynne Rd., Memphis, Tenn. 38117

[21] Appl. No.: 552,078

[22] Filed: Jul. 13, 1990

[51] Int. Cl.$^5$ ............................................. B60Q 1/00
[52] U.S. Cl. .................... 340/450; 340/438; 340/623; 73/447; 73/453; 73/440
[58] Field of Search ............ 340/425.5, 438, 450, 340/450.3, 457, 623, 631; 324/425; 73/32 R, 291, 440, 447, 451, 453

[56] References Cited

U.S. PATENT DOCUMENTS

| | | | |
|---|---|---|---|
| 1,556,185 | 10/1925 | Walker | 73/440 |
| 2,922,300 | 1/1960 | Woods | 73/440 |
| 3,777,574 | 12/1973 | Brown | 73/453 |
| 3,947,813 | 3/1976 | Uemura et al. | |
| 3,954,010 | 5/1976 | Hilblom | 73/291 |
| 4,003,255 | 1/1977 | Spencer | 73/194 |
| 4,020,481 | 4/1977 | Nakagawa | |
| 4,107,493 | 8/1978 | Nagara et al. | 200/84 |
| 4,350,885 | 9/1982 | Patis | 250/231 |
| 4,400,978 | 8/1983 | Guay et al. | 73/453 |
| 4,697,454 | 10/1987 | Lu | 73/440 |
| 4,736,628 | 4/1988 | Lin | 73/440 |
| 4,833,441 | 5/1989 | Okada et al. | 340/450 |
| 4,843,193 | 6/1989 | Budecker et al. | 200/84 |

Primary Examiner—Donnie L. Crosland
Assistant Examiner—Brent A. Swarthout
Attorney, Agent, or Firm—Walker & McKenzie

[57] ABSTRACT

A vehicle anti-freeze monitor for monitoring the capability of the vehicle's coolant mixture in the cooling system of the vehicle to resist freezing. The monitor includes a light emitting diode, a reed switch for coupling the indicator to a source of electricity and for selectively activating and deactivating the indicator. Also included is a float for submersion into the vehicle's coolant mixture. The float includes a buoyant body and a magnet which activates the reed switch when the vehicle's coolant mixture is in a safe condition against freezing and deactivates the reed switch when the coolant mixture is in an unsafe freezable condition.

11 Claims, 2 Drawing Sheets

VEHICLE ANTI-FREEZE MONITOR

BACKGROUND OF THE INVENTION

1. Field of the Invention

This invention relates to a vehicle anti-freeze monitor for monitoring the capability of the vehicle's coolant mixture in the cooling system of the vehicle to resist freezing.

2. Information Disclosure Statement

A preliminary patentability search in Class 340, subclass 624 revealed the following patents: Brown et al, U.S. Pat. No. 3,777,574; Uemura et al, U.S. Pat. No. 3,947,813; Hilblom, U.S. Pat. No. 3,954,010; Spencer, U.S. Pat. No. 4,003,255; Nakagawa, U.S. Pat. No. 4,020,481; Nagara et al, U.S. Pat. No. 4,107,493; Patis, U.S. Pat. No. 4,350,885; Guay et al, U.S. Pat. No. 4,400,978; Okada et al, U.S. Pat. No. 4,833,441 and Budecker et at, U.S. Pat. No. 4,843,193.

The Brown et al patent discloses a specific gravity sensor of the type in which a beam of light is interrupted by a light-flow inhibitor which lowers in liquid when the specific gravity of the liquid decreases.

The Uemura et al patent discloses a liquid level reduction alarm device for a liquid reservoir vessel kept in liquid communication with a brake master cylinder for delivery of an alarm signal to the vehicle driver if the liquid level in the reservoir vessel should reduce to an excessive degree so as to warn the driver to replenish the brake oil.

The Hilblom patent discloses a combined visual and electronic liquid indicator which may be used as a battery hydrometer, which also operates on the principle of either a visual indication of the specific gravity or an electronic indication by the use of a float ball as a shutter between the light source and the light detector.

The Spencer patent is a method and apparatus for measuring fluid flow and controlling fluid flow systems by the use of a magnetically responsive float. Also the system can be employed to determine fluid viscosity.

The Nakagawa patent discloses a fluid level alarm device for use with automotive vehicles for informing the operator of the vehicle of a reduction below a certain level of an operating fluid stored in the fluid tank associated with a master cylinder to serve the purpose of preventing any resultant failure in operation of the master cylinder. The alarm device operates by positioning a magnetically operable reed switch, electrically connected to an alarm, so when the fluid stored in the tank is lowered below a specified level, the reed switch is magnetically closed to operate the alarm.

The nagara et al patent discloses a radiator cap which includes a float engaged with the cap body so as to move up and down in accordance with the level of the coolant. A reed switch secured to the cap body is opened or closed in response to movement of the float so that the reed switch actuates suitable warning means when the liquid level is too low.

The Patis patent discloses a battery hydrometer which provides an analog output electrical signal related to the specific gravity of the battery electrolyte.

The Guay et al patent discloses an electronic hydrometer having an electronic circuit capable of automatically controlling the position of a float by means of a variable current supply and providing an output signal indicative of the density of the liquid.

The Okada et al patent discloses a reservoir for the coolant of the radiator of a automobile and includes a reed switch for warning that the level of liquid contained in the reservoir is below a prescribed level. A float is included having a magnet to close the reed switch.

The Budecker et al patent discloses a reservoir for a hydraulic brake system provided with a screw coupling and a reservoir telltale sounding device.

In addition, it should be pointed out that the determination of an automobile's anti-freeze protection has thus far remained a somewhat laborious process of manually opening into the cooling system, extracting a sample of coolant fluid, and inspecting a visual hydrometer. This hydrometer usually consists of floating elastomeric balls which are calibrated to float at various densities of coolant fluid, thus providing a visual measurement of the freezing point of the solution. Today's automobiles generally run considerably hotter than formerly and require some method to provide for the resulting expansion of the coolant liquid. An overflow tank is now commonly used. It collects the coolant as it expands out of the radiator in its superheated phase and provides an escape mechanism whereby the fluid may subsequently be withdrawn back into the cooling system as the engine cools down. Gaining access to the coolant liquid by manual extraction is laborious and sometimes dangerous.

A variety of electronic hydrometers for measuring the specific gravity of electrolytes with opto-isolation techniques is well known in the art. The difficulties of constructing light emitting and light detecting circuitry with complex housing and lenses have thus far failed to satisfy the need of a simple device suitable for placement within an automobile coolant system.

None of the above mentioned prior art discloses or suggests the present invention. More specifically, none discloses or suggests a vehicle anti-freeze monitor for monitoring the capability of the vehicle's coolant mixture in the cooling system of the vehicle to resist freezing, comprising: indicator means; switch means movable between first and second positions for respectively selectively activating and deactivating said indicator means; and means for submersion in the vehicle's coolant mixture for moving said switch means to said first position when the specific gravity of the vehicle's coolant mixture is greater than a selected certain specific gravity corresponding to the lowest temperature point of a base coolant mixture above which the base coolant mixture is considered to be safe a to its capability of resisting freezing to activate said indicator means, and for moving said switch means to said second position when the specific gravity of the vehicle's coolant mixture is below said selected certain specific gravity to deactivate said indicator means.

SUMMARY OF THE INVENTION

The present invention provides an improved means for monitoring the capability of the vehicle's coolant mixture in the cooling system of the vehicle to resist freezing without having to manually extract a sample of the coolant fluid for inspection with a visual hydrometer and without the need of complex light emitting and light detecting devices.

Thus, one of the objects of the present invention is to provide a simple yet effective anti-freeze monitor for monitoring the capability of the vehicle's coolant mixture in the cooling system of the vehicle to resist freezing and without requiring the removal of a sample of coolant from the system.

A further object is to provide a means for monitoring automobile coolant anti-freeze protection through a device disposed in the coolant expansion tank with a very simple monitoring device to achieve this goal.

A further object is to provide such a vehicle anti-freeze monitor which eliminates the necessity for opto-isolation techniques.

A further object is to provide such a vehicle anti-freeze monitor which may be easily removed from the system for cleaning.

A further object is to provide such a vehicle anti-freeze monitor which includes a warning device when the battery or electrical circuit is functioning improperly and also provides a visible signal when the anti-freeze mixture is inadequate.

A further object is to provide such a vehicle anti-freeze monitor which is capable of withstanding the high temperatures of the vehicle's coolant mixture.

DESCRIPTION OF THE PREFERRED EMBODIMENT

Figure 1:
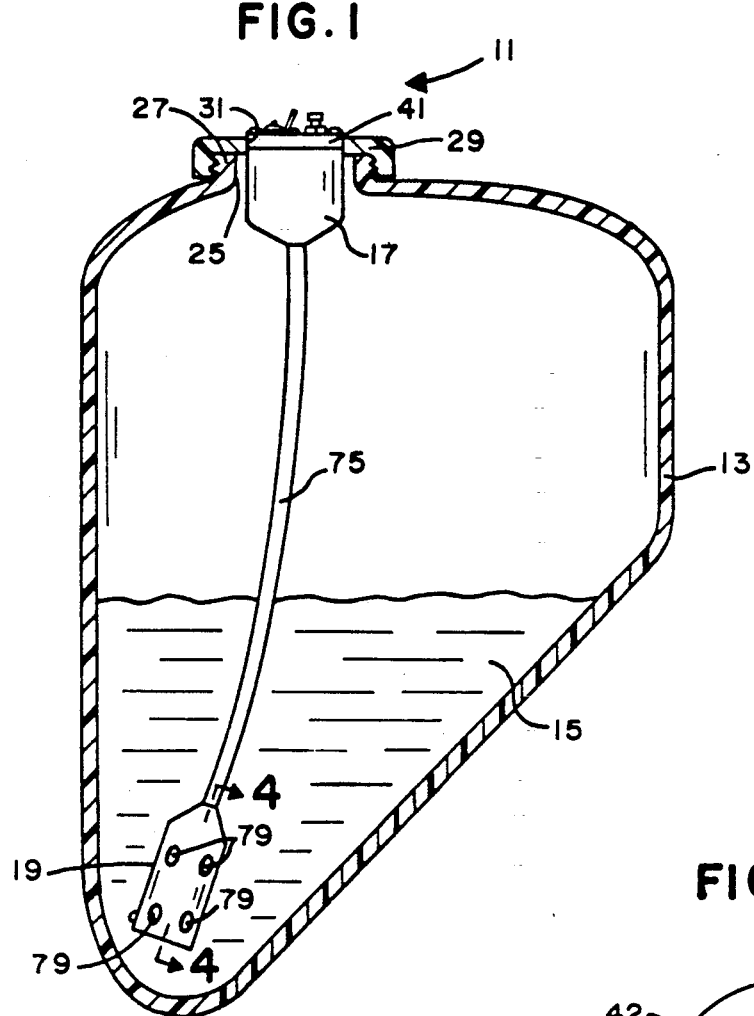
FIG. 1 is an elevational view of the vehicle anti-freeze monitor of the present invention shown as installed in the coolant expansion tank of the vehicle and with the coolant tank being viewed in section as along a vertical plane therethrough.
Figure 2:
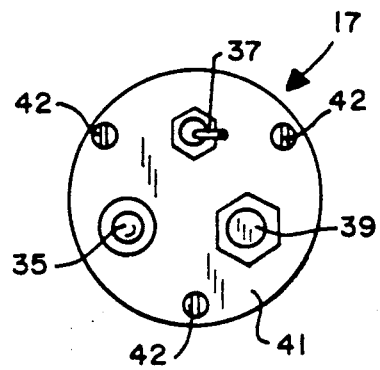
FIG. 2 is a top view of the upper body member of the anti-freeze monitor of the present invention.

The vehicle anti-freeze monitor of the present invention is particularly adapted to be used in the coolant expansion tank which is part of the water cooling system of a vehicle, not shown. The coolant expansion tank 13 is well known to those skilled in the art and contains the vehicle's coolant mixture 15 of water and anti-freeze liquid. Such coolant expansion tanks vary in size and shape for different vehicles, and are usually provided with an opening, not shown, for the filling thereof and provided with hoses or the like connecting the expansion tank to the vehicle's radiator, not shown, as is known by those skilled in the art. Also, as is known by those skilled in the art, the anti-freeze liquid is normally ethylene glycol, and the water/ethylene glycol solution frequently used for general anti-freeze protection is a 50% mixture of each which provides protection from freezing to minus 35 degrees Fahrenheit. Also, as is known, ethylene glycol has a specific gravity of approximately 1.144, and the 50% mixture of water and ethylene glycol has a specific gravity of 1.072.

In general, monitor 11 includes a hollow upper body member 17, a hollow lower body member 19 having an inner chamber 21, and float means 23 movably mounted in inner chamber 21 for movement upwardly and downwardly relative to lower body member 19 responsive to specific gravity changes in the coolant mixture 15.

In use, monitor 11 is mounted on tank 13, preferably as shown in FIG. 1, wherein it will be seen tank 13 has an opening 25 surrounded by an externally threaded neck portion 27 on which is threadably mounted a cap 29 having a central aperture 31. Upper body member 17 extends through aperture 31 and is fixedly mounted therein by suitable means well known to those skilled in the art, as for example, by being made an integral part of cap 29 or by adhesives or the like joining upper body member 17 to cap 29.

A battery 33 is preferably, although not necessarily, mounted in the interior of hollow body member 17 and may be of long shelf life, as for example a 3 volt lithium battery. Indicator means, such as a light emitting diode 35 (hereinafter sometimes referred to as LED 35), a first switch 37, which is preferably a single pole—single throw type of switch, and a push button switch 39 are respectively mounted on top 41 of upper body member 17. Top 41 is preferably removably mounted as by means of screws 42. The LED 35 and switches 37, 39 are mounted in such a manner on top 41 that the light from the diode is emitted outwardly from the top and the switches 37, 39 are accessible from the outside of upper body member 17. The lower portions of the LED 35 and switches 37, 39 preferably extend downwardly through openings, not shown, in top 41 so the electrical connections in the hereinafter described electrical circuit means can be accomplished.

Figure 3:
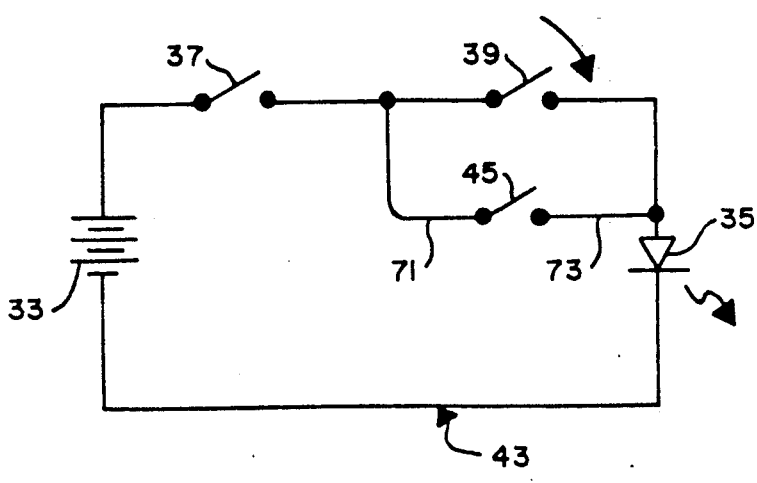
FIG. 3 is a schematic view of the electrical system of the anti-freeze monitor.

The electrical circuit means 43 for electrically coupling battery 33 and LED 35 is best seen in FIG. 3. Thus, it will be seen that first switch 37 is interposed in electrical circuit means 43 and movable between an open position in which electricity from battery 33 is prevented from passing from the battery to the LED 35 and a closed position in which electricity is allowed to pass from the battery to the LED 35 for the energizing of the light emitting diode.

Switch means for selectively activating and deactivating LED 35, as for example, a proximity switch, such as a reed switch 45, well known to those skilled in the art, is fixedly mounted in lower body member 19 in a fixed position of alignment relative to the lower body member. Reed switch 45 is interposed in electrical circuit means 43 between first switch 37 and LED 35 and movable between a first or open position in which electricity from battery 33 is prevented from passing from the battery to the light emitting diode and a second or closed position in which electricity is allowed to pass from the battery to the light emitting diode for the energizing of the light emitting diode when the first switch 37 is in said closed position.

Push button switch means 39, which is normally open, is interposed in circuit means 43 in parallel with reed switch 45 and movable between the normally open position and a closed position when manually pushed downwardly. When switch means 39 is in said open position electricity from battery 33 is prevented from passing from the battery to the light emitting diode when the reed switch 45 is open. When switch means 39 is in said closed position electricity is normally allowed to pass from battery 33 to the LED 35 for the energizing of the light emitting diode when first switch 37 is closed. The switch means 39 is used to check the proper operation of the circuit as will be understood more fully in the description thereof to follow later in the specification. Float means 23 includes a buoyant body 47 and magnet means 49 attached to buoyant body 47. Buoyant body 47 is preferably hollow in the interior thereof as at 51 with the hollow portion 51 being completely enclosed by the outer portion of the buoyant body 47. Also, buoyant body 47 is preferably cylindrical and includes a top portion 53, a bottom portion 55, and a cylindrical side portion 57 integrally interconnecting top portion 53 and bottom portion 55.

Magnet means 49 is preferably an elongated permanent bar magnet which is preferably embedded in the top portion 53 of buoyant body 47 and extends transversely across the buoyant body. Also it should be pointed out that magnet means 49 is preferably in parallel relationship to reed switch 45 for the effective operation of the reed switch 45 when magnet means 49 is in proximity thereto. It is kept in such alignment by suitable means, as a vertical rib 59 provided on buoyant body 47 and extending into inner chamber 21, and by a vertical notch 61 provided in side portion 57 of buoyant body 47 which slidably engages rib 59 to prevent turning of float means 23 about a vertical axis.

Figure 4:
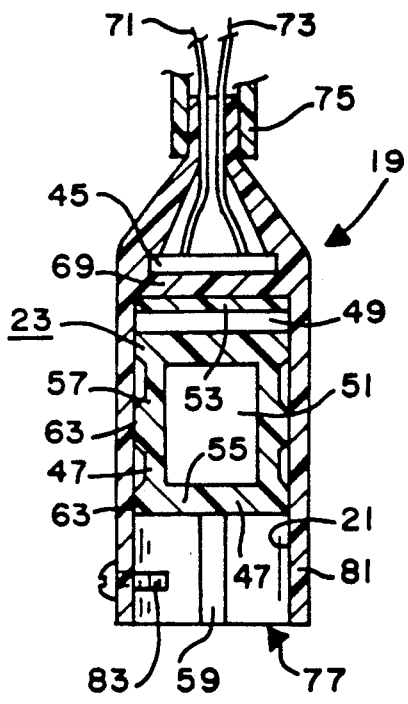
FIG. 4 is a sectional view of the lower body member of the monitor taken as on a vertical plane through the longitudinal center line thereof and with the float being shown in an upper position.
Figure 5:
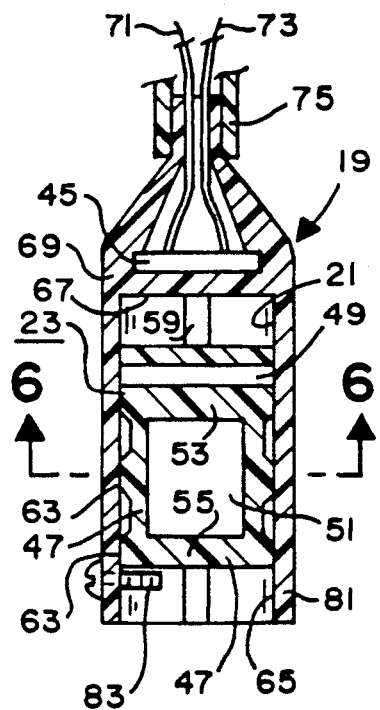
FIG. 5 is a view similar to FIG. 4, but showing the float in a lower position.
Figure 6:
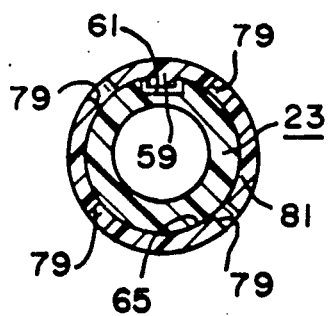
FIG. 6 is a sectional view taken as on the lines 6—6 of FIG. 5.

Buoyant body 47 is preferably spool-like in construction with circular portions 63 which extend outwardly from the main body of sides 57 and slidably engage the cylindrical inner wall surface 65 of lower body member 19 that in part defines inner chamber 21. The top part of inner chamber 21 is defined by the lower surface 67 of the upper wall portion 69 of lower body member 19. Reed switch 45 is preferably embedded in upper wall 69 with the insulated electrical wires 71, 73 attached to reed switch 45 extending outwardly through the open upper end of lower body member 19, as best seen in FIGS. 4 and 5. It will be understood that wires 71, 73 form a part of electrical circuit means 43 and extend to upper body member 17 where they are connected into the remainder of the electrical circuit means as best seen in FIG. 3. A plastic sheath 75 preferably is provided over the portions of the wires 71, 73 that extend between lower body member 19 and upper body member 17.

Inner chamber 21 preferably opens downwardly through the opened lower end 77 of lower body member 19. A plurality of holes 79 are provided through the cylindrical side wall 81 of lower body member 19, which prevents any air lock of the float means 23 and provides free and easy movement of the float means with any changes in the specific gravity of the coolant mixture 15. A stop of any suitable construction such as a screw 83 threadedly received in a threaded aperture through wall 81, limits downward movement of float means 23 beyond a certain point, as shown in FIG. 5. Float means 23 is limited in its upward movement by the engagement of top portion 53 with upper wall 69, as shown in FIG. 4.

The material of the upper body member 17, lower body member 19, and buoyant body 47 is preferably an acetal resin, such as "DELRIN" (a registered trademark of E.I. DuPont DeNemours & Co., Inc.) so that the parts will withstand the heat and the coolant mixture composition.

The weight, size, and material of buoyant body 47 and magnet means 49 is selected so that float means 23 floats in the particular base coolant mixture selected, which in this case is a coolant mixture of 50% water and 50% ethylene glycol, and sinks at any lesser concentration. In other words the float means 23 will float when the concentration of ethylene-water mixture is adequate for anti-freeze purposes, which in the use of a 50% mixture of water and ethylene-glycol will provide protection from freezing to minus 35 degrees Fahrenheit.

Stated another way, the float means is made to have a certain selected specific gravity, namely 1.072 in the example given, corresponding to the lowest temperature point of said base coolant mixture above which the base coolant mixture is considered to be safe as to its capability of resisting freezing. Thus, when the specific gravity of the vehicle's coolant mixture 15 is greater than said certain specific gravity, float means 23 rises to a position in which magnet means 49 is in proximity to the reed switch 45 to activate LED 35 and indicate that the vehicle's coolant mixture 15 is in a safe condition against freezing when the temperature of the vehicle's coolant mixture is above said lowest temperature point. It will be understood that the above mentioned example of a 50% mixture as the base coolant mixture giving a protection at minus 35 degrees is used in most places but in extremely cold places a 75% ethylene-glycol/25% water mixture can be used. In other words, the float means 23 may be made with a different specific gravity, as desired, without departing from the spirit and scope of the present invention.

Thus, it will be understood that in practice when the anti-freeze protection is adequate, float means 23 rises to a position in which magnet means 49 is in proximity to the proximity reed switch 45 and closes the reed switch.

During periods when the user is not checking for the adequacy of the coolant mixture 15, first switch 37 is kept in an open position so as not to drain the battery 33. On the other hand, when the user desires to check the coolant mixture 15, first switch 37 is closed and if the float means 23 is in the upper position mentioned above and as shown in FIG. 4, the electrical energy is allowed to flow through LED 5 providing a visual signal that the coolant mixture is satisfactory. However, if first switch 37 is closed and the LED 35 does not light up, either (1) the electrical circuit is not functioning properly, i.e., LED 35 is not functioning or (2) the battery 33 is dead. Thus, when first switch 37 is closed for testing coolant mixture 15 as to its capability of resisting freezing and the LED 35 does not light up, then in order for the operator to be certain that the entire electrical circuit is functioning properly, push button switch 39 can be closed thus sending current directly through the LED 35. If the light emitting diode fails to light, then this would provide an indication that either the battery 33 is dead or the LED 35 is not functioning. On the other hand, if upon closure of push button switch 39 the LED 35 does light up, having previously failed to do so upon closure of switch 39, then the operator can be assured that the electrical circuitry is intact and the fault lies purely in the inadequacy of the coolant mixture 15. The float means 23 has sunk to a position out of proximity to reed switch 45, as shown in FIG. 5 to indicate that the coolant mixture is inadequate, that is, is in an unsafe freezable condition below said lowest temperature point.

It will be understood that in the operation of the monitor 11, the monitor is disposed in tank 13 as previously described and as shown in FIG. 1 with the lower body member 19 being adjacent the bottom of the tank so the lower body member is submerged in the coolant mixture 15.

Although the present invention has been described and illustrated with respect to a preferred embodiment thereof, it is not to be so limited since modifications and changes can be made therein which are within the full intended scope of the invention.

I claim:

1. A vehicle anti-freeze monitor for monitoring the capability of the vehicle's coolant mixture in the cooling system of the vehicle to resist freezing, said monitor comprising:
   a) indicator means;
   b) proximity switch means for coupling said indicator means to a source of electricity and for selectively activating and deactivating said indicator means; and
   c) float means for submersion in the vehicle's coolant mixture, said float means including a buoyant body and magnet means attached to said buoyant body, said float means being floatable upwardly to a position in proximity to said proximity switch means for the activation of said proximity switch means by said magnet means, said float means having a certain selected specific gravity corresponding to the lowest temperature point of a base coolant mixture above which the base coolant mixture is considered to be safe as to its capability of resisting freezing whereby when the specific gravity of the vehicle's coolant mixture is greater than said certain specific gravity, said float means rises to a position in which said magnet means is in proximity to said proximity switch means to activate said indicator means and indicate that the vehicle's coolant mixture is in a safe condition against freezing when the temperature of the vehicle's coolant mixture is above said lowest temperature point.

2. The vehicle anti-freeze monitor of claim 1 in which is included an upper body member and a lower body member, and in which is included a source of electricity, said indicator means being mounted in said upper body member; said float means, said magnet means and said proximity switch means being mounted in said lower body member.

3. The vehicle anti-freeze monitor of claim 1 or claim 2 in which said proximity switch means is a reed switch and in which said monitor includes means for maintaining alignment of said magnet means with said reed switch.

4. The vehicle anti-freeze monitor of claim 3 in which said monitor includes push button switch means coupled to said source of electricity and to said indicator means for testing to determine if said source of electricity and said indicator means are operative.

5. The vehicle anti-freeze monitor of claim 3 in which said lower body member has a vertical inner chamber and said lower body member has openings through the sides thereof for allowing free flow of the coolant mixture between said inner chamber and the exterior of said lower body member, and in which said float means is movably mounted in said inner chamber.

6. The combination with a vehicle's water cooling system of an anti-freeze monitor for monitoring the capability of the vehicle's coolant mixture t resist freezing, said water cooling system including a coolant expansion tank for containing the vehicle's coolant mixture of water and anti-freeze liquid therein, said tank including an aperture, said monitor being mounted on said tank and extending into the interior of said tank through said aperture; said monitor comprising:
   a) a source of electricity;
   b) indicator means operably coupled to said source of electricity;
   c) proximity switch means operably interposed between said source of electricity and said indicator means for selectively activating and deactivating said indicator means;
   d) float means for submersion in the vehicle's cool in said tank, said float means including a buoyant body and magnet means attached to said buoyant body, said float means being floatable upwardly to a position in proximity to said proximity switch means for the activation of said proximity switch means by said magnet means, said float means having a certain selected specific gravity corresponding to the lowest temperature point of a base coolant mixture above which the base coolant mixture is considered to be safe as to its capability of resisting freezing whereby when the specific gravity of the vehicle's coolant mixture is greater than said certain specific gravity, said float means rises to al position in which said magnet means is in proximity to said proximity switch means to activate said indicator means and indicate that the vehicle's coolant mixture is in a safe condition against freezing when the temperature of the vehicle's coolant mixture is above said lowest temperature point.

7. The combination with a vehicle's water cooling system of an anti-freeze monitor for monitoring the capability of the vehicle's coolant mixture to resist freezing, said water cooling system including a coolant expansion tank for containing the vehicle's coolant mixture of water and anti-freeze liquid therein, said tank including an aperture, said monitor being mounted on said tank and extending into the interior of said tank through said aperture; said monitor comprising:
   a) indicator means;
   b) switch means movable between first and second positions for respectively selectively activating and deactivating said indicator means; and
   c) means for submersion in the vehicle's coolant mixture for moving said switch means to said first position when the specific gravity of the vehicle's coolant mixture is greater than a selected certain specific gravity corresponding to the lowest temperature point of a base coolant mixture above which the base coolant mixture is considered to be safe as to its capability of resisting freezing to activate said indicator means and for moving said switch means to said second position when the specific gravity of the vehicle's coolant mixture is below said selected certain specific gravity to deactivate said indicator means.

8. The combination with a vehicle's water cooling system of an anti-freeze monitor for monitoring the capability of the vehicle's coolant mixture to resist freezing, said water cooling system including a coolant expansion tank for containing the vehicle's coolant mixture of water and anti-freeze liquid therein, said tank including an aperture, said monitor being mounted on said tank and extending into the interior of said tank through said aperture; said monitor comprising:
   a) a hollow upper body member mounted on said tank in said aperture;
   b) a battery mounted in said upper body member;
   c) a light emitting diode mounted on said upper body member;
   d) electrical circuit means for electrically coupling said battery and said light emitting diode;
   d) a first switch means mounted on said upper body member and interposed in said electrical circuit means and movable between an open position in which electricity from said battery is prevented from passing from said battery to said light emitting diode and a closed position in which electricity is allowed to pass from said battery to said light emitting diode for the energizing of said light emitting diode;

e) a hollow lower body member submerged in the vehicle's coolant mixture, said lower body member having a vertical inner chamber and having openings through the sides thereof allowing free flow of the vehicle's coolant mixture between said inner chamber and the exterior of said lower body member;

f) a reed switch fixedly mounted in said lower body member in a fixed position of alignment relative to said hollow lower body member and interposed in said electrical circuit means between said first switch means and said light emitting diode and movable between an open position in which electricity from said battery is prevented from passing from said battery to said light emitting diode and a closed position in which electricity is allowed to pass from said battery to said light emitting diode for the energizing of said light emitting diode when said first switch means is in said closed position;

g) float means movably mounted in said inner chamber of said hollow lower body member for movement upwardly and downwardly relative to said body member responsive to specific gravity changes of the vehicle's coolant mixture, said float means including a buoyant body and magnet means attached to said buoyant body, said float means being floatable upwardly to a position in proximity to said reed switch for the movement of said reed switch to said closed position by said magnet means to energize said light emitting diode and being sinkable downwardly to a position in which said magnet means is out of proximity to said reed switch for the movement of said reed switch to said open position to prevent electricity from said battery from passing to said light emitting diode, said float means having a certain selected specific gravity corresponding to the lowest temperature point of a base coolant mixture above which the base coolant mixture is considered to be safe as to its capability of resisting freezing whereby when the specific gravity of the vehicle's coolant mixture is greater than said certain specific gravity said float means rises to a position in which said magnet means is in proximity to said reed switch to energize light emitting diode and indicate that the vehicle's coolant mixture is in a safe condition against freezing when the temperature of the vehicle's coolant mixture is above said lowest temperature point, and when the specific gravity of the vehicle's coolant mixture is less than said certain specific gravity said float means sinks to a position in which said magnet means is out of proximity to said reed switch to prevent electricity from said battery to pass to said light emitting diode and indicate that the vehicle's coolant mixture is in an unsafe freezable condition below said lowest temperature point.

9. The combination of claim 8 in which said monitor includes push button switch means interposed in said circuit means in parallel with said reed switch means and mounted on said upper body member and movable between an open position in which electricity from said battery is prevented from passing from said battery to said light emitting diode when said reed switch is open and a closed position in which electricity is allowed, to pass from said battery to said light emitting diode (LED) for the energizing of said light emitting diode when said first switch means is closed to check said battery and LED and indicate that said battery and LED are functioning properly.

10. The combination of claim 9 which includes alignment means operably coupled between said lower body member and said float means for maintaining said magnet means aligned in parallel relationship with said reed switch.

11. The combination of claim 10 in which upper and lower body members are formed of an acetal resin.

* * * * *